United States Patent [19]
Galun et al.

[11] Patent Number: 5,919,763
[45] Date of Patent: Jul. 6, 1999

[54] IL-6/SIL-6R COMPLEX FOR PROMOTION OF LIVER FUNCTIONS

[75] Inventors: Eithan Galun, Har Adar, Israel; Stefan Rose-John; Malte Peters, both of Mainz, Germany

[73] Assignee: Hadasit Medical Research Services and Development Company Ltd., Jerusalem, Israel

[21] Appl. No.: 09/087,796

[22] Filed: Jun. 1, 1998

[51] Int. Cl.[6] ........................................... A61K 38/00
[52] U.S. Cl. ................... 514/12; 514/2; 514/893; 514/894; 530/351; 424/85.1; 424/85.2
[58] Field of Search ................... 424/85.1, 85.2; 514/893, 894, 2, 12; 530/351

[56] References Cited

PUBLICATIONS

Medline on 97187685, Fischer et al., *Nature Biotech.,* 15(2), 142–5. (abstract), Feb. 1997.

*Primary Examiner*—Cecilia J. Tsang
*Assistant Examiner*—C. Delacroix-Muirheid
*Attorney, Agent, or Firm*—Mark M. Friedman

[57] ABSTRACT

A method for treating an injury of a liver of a subject with a composition featuring a pharmaceutically acceptable amount of an IL-6/sIL-6R complex, preferably Hyper-IL-6. The composition is administered to the subject such that the injury to the liver is treated.

7 Claims, 5 Drawing Sheets

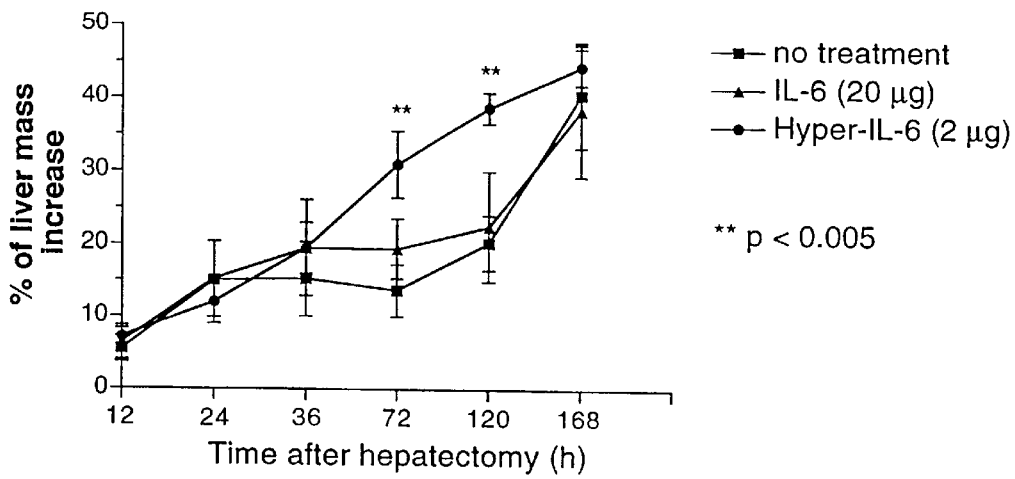

FIGURE 1

Figure 1: *Hyper-IL-6 causes an accelerated reconstitution of the liver weight following partial hepatectomy.*

Immediatedly following a 50% partial hepatectomy, IL-6 (20μg/mouse), or Hyper-IL6 (2 μg/mouse), or physiological saline was injected intraperitoneally into mice. At the time points indicated in the figure, mice were sacrificed, the remnant livers were removed and the percentage of liver weight increase compared to time 0 at hepatectomy was determined (see Methods). Four to six mice were operated at each time point in each treatment group. Mean values ± standard deviations are presented.

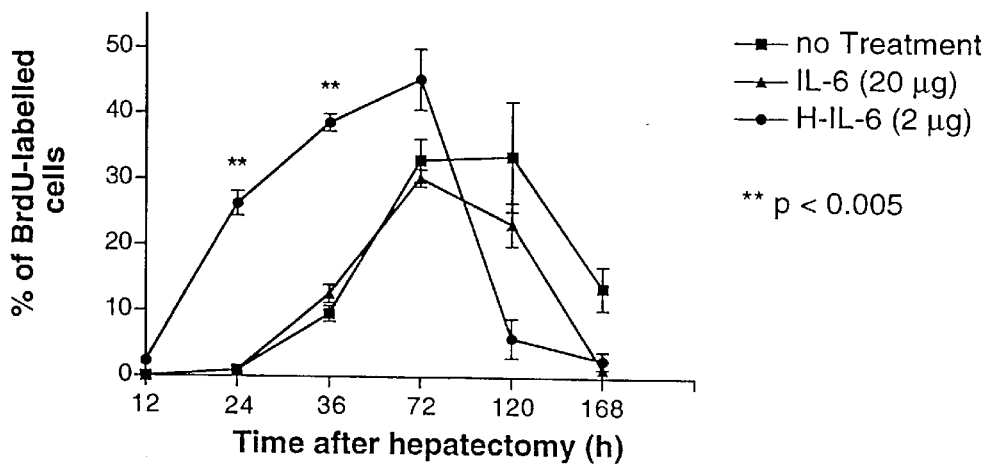

FIGURE 2

Figure 2: *Hyper-IL-6 significantly accelerates liver proliferation in mice following partial hepatectomy in mice.*

Following a 50% partial hepatectomy, IL-6 (20 μg/mouse), or Hyper-IL-6 (2 μg/mouse), or physiological saline was injected intraperitoneally into mice. One hour before the mice were sacrificed, 50 mg/kg body weight BrdU in PBS was injected intraperitoneally into the mice. After removal of the remnant livers, the organs were fixed in 4% formaldehyde and embedded in paraffin. Tissue sections were subjected to BrdU immunhistochemistry. The percentage of BrdU-positive nuclei were counted in at least three mice per treatment group. Mean values ± standard deviation are shown.

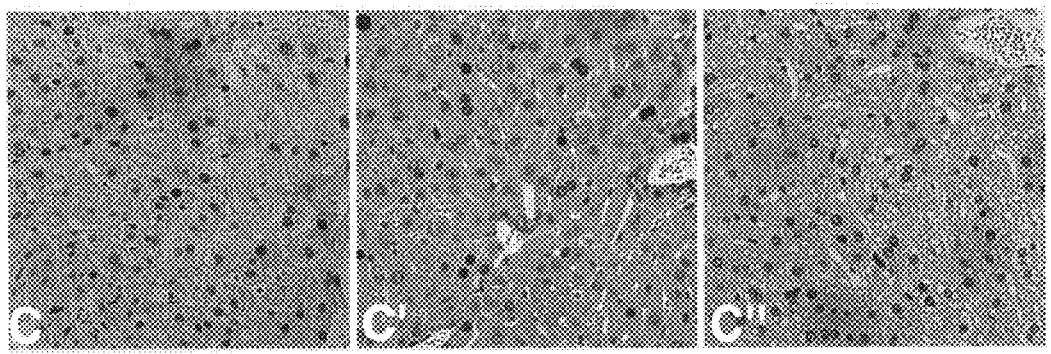

FIGURE 3 (continued)

Figure 3: *BrdU labelling following partial hepatectomy in mice.*
Immunohistochemical detection of BrdU incorporation in S-phase liver nuclei as an indicator of liver cell proliferation. Following 50% partial hepatectomy, mice were either left untreated (A-C), treated with 20 μg IL-6/mouse (A'-C'), or treated with 2 μg Hyper-IL-6 (A"-C"). Mice were sacrificed 24 hours (A, A', A"), 36 hours (B, B', B"), or 120 hours (C, C', C") following surgery. One hour before the animals were sacrificed 50 mg/kg body weight BrdU in PBS was injected intraperitoneally. The bars represent 100 μm.

No Hepatectomy

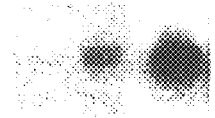

C    IL-6    H-IL-6

24 h post Hepatectomy

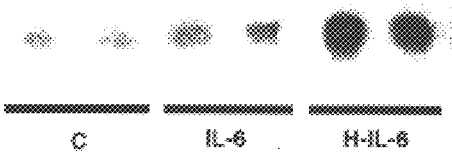

*Figure 4: The acute phase response is intact in mice following partial hapatectomy.*

Upper panel: 24 hours after intraperitoneal injection of saline, 20 μg IL-6 alone, or 2 μg Hyper-IL-6, blood was drawn from the animals which did not undergo partial hepatectomy. One μl of the murine serum was loaded on a 12.5 % SDS gel and was subjected to SDS-PAGE. The gel was blotted onto a nitrocellulose membrane and was subjected to Western blotting using a monoclonal antibody specific for murine haptoglobin.

Lower panel: Mice that had undergone partial hepatectomy were immediately treated with either saline, 20 μg IL-6, or with 2 μg Hyper-IL-6. 24 hours after the operation, blood was drawn from the animals and serum was subjected to Western blotting as described above.

IL-6/SIL-6R COMPLEX FOR PROMOTION OF LIVER FUNCTIONS

FIELD AND BACKGROUND

The present invention relates to a novel method for promoting liver regeneration, and in particular to a method using a composition featuring the IL-6/sIL-6R complex for promoting liver cell proliferation and liver weight restoration, as well as the restoration of liver functions.

The loss of liver functions from traumatic or toxic injury or disease may cause severe debilitation or even death. There are many causes for the loss of liver functions, including malignancies in the liver, both primary and those which metastasize to the liver from another location in the body, viral diseases such as the many forms of viral Hepatitis, and hepatotoxicity caused by exposure to excessive liver toxins such as drug overdose and pesticides. Indeed, even some normally non-toxic substances can become hepatotoxic when abused, such as paracetamol and ethanol. Thus, injury to the liver, resulting in the loss of liver functions, can have many different initial causes.

Patients with acute liver failure have high morbidity and mortality rates. Only 40% of patients treated with conservative medical treatment alone survive. Those patients which do survive are somehow able to restore liver functions. Among the essential functions of the liver are glucose regulation, synthesis of many blood proteins like albumin and coagulation proteins, secretion of bile, biodegradation of toxic compounds, and others[1] (see Appendix for a complete list of references). Little if any disturbance is observed in these functions when only 33% of the liver remains intact and 90% of the remaining cells undergo proliferation and regeneration[1].

Liver regeneration is important for the restoration of liver functions in response to injury, either disease or trauma induced. The term "liver regeneration" is defined as an orchestrated response induced by specific external stimuli and involving sequential changes in gene expression, growth factor production, and morphological structure[1]. Studies have shown that when rats are joined in pairs through parabiotic circulation, hepatectomy of one member of the pair causes regeneration of the intact liver of the other member, with the maximum effect seen when the liver of one animal is totally removed[2,3]. As demonstrated by these and other studies, many soluble factors, such as multiple growth factors and cytokines, are mitogenic signals for hepatocytes during liver regeneration.

Several lines of evidence suggest that TNF-α (Tumor necrosis factor alpha) and IL-6 (Interleukin-6) are the most crucial components of the early signaling pathways leading to regeneration. IL-6 is secreted by Kupffer cells, and this secretion is stimulated by TNF-α. IL-6 is an important signal for the initiation of acute phase protein synthesis by hepatocytes as a part of the overall inflammatory response[4]. Recent experiments have demonstrated that liver regeneration following partial hepatectomy (pHx) is massively impaired in mice carrying a homozygous deletion of the IL-6 gene[8] or of the TNF-α type I receptor gene[9]. Furthermore, the plasma IL-6 concentration increases after pHx (partial hepatectomy), reaching high levels by 24 hours after the removal of liver tissue[5-7]. Thus, IL-6 and TNF-α are important components of the response to liver injury.

On target cells, IL-6 first binds to a specific IL-6 receptor[12]. This IL-6/sIL-6R complex induces the homodimerization of two gp130 signal transducing molecules[13,14] leading to intracellular signaling events. Soluble forms of the IL-6R (sIL-6R) are generated by limited proteolysis from the cell surface[15] and render cells which do not express membrane bound IL-6R responsive towards IL-6[16]. Furthermore, sIL-6R acts as a serum-binding protein for IL-6 and prolongs the plasma half-life of IL-6[17]. The presence of the IL6/sIL-6R complex in IL-6/sIL-6R double transgenic mice leads to a marked extramedullary expansion of hematopoietic progenitor cells[18]. The presence of IL-6 alone does not cause similar effects. Thus, the IL-6/sIL-6R appears to have certain effects which extend beyond those of IL-6 alone.

Unfortunately, in spite of many published findings regarding the effects of IL-6 and other molecular components of the liver regeneration pathway, few suitable treatments are available for those suffering from a loss of liver functions. Liver transplantation is the only established therapy which has been shown to improve the survival rate of patients with acute liver failure. However, transplantation is a time consuming and costly therapy associated with a life-long requirement for immunosuppression. Long-term side-effects of the immunosuppression remain unevaluated. In addition, as for any type of organ transplantation, suitable donors are not always available.

Therapies based on the molecular basis of liver regeneration have been examined in an attempt to the development of new treatment strategies beyond liver transplantation. For example, experiments in which recombinant HGF (hepatocyte growth factor) was administered to animals following liver injury suggested that the administration of HGF might be beneficial in liver regeneration and that HGF might help to improve the regenerating capacity of the liver[29-33]. However, since the plasma half-life of HGF is extremely short (t 1/2 of 4.5 min), HGF must be administered by a continuous infusion into a peripheral vein or into the portal vein. Such inconveniently frequent administration is a severe drawback to HGF treatment.

There is therefore a need for, and it would be useful to have, a novel treatment for liver injury which would promote the restoration of liver functions in a subject by promoting and enhancing liver regeneration.

SUMMARY OF THE INVENTION

It is one object of the present invention to provide a treatment for the promotion of liver regeneration and the restoration of liver functions in a subject suffering from liver injury.

It is another object of the present invention to provide such a treatment which is effective on the molecular level, through the stimulation of the endogeneous liver regeneration pathways and mechanisms of the subject.

It is still another object of the present invention to provide such a treatment through the provision of a pharmaceutically effective composition which features the IL-6/sIL-6R complex.

It is yet another object of the present invention to provide such a composition which includes Hyper-IL-6.

These and other objects of the present invention are explained in greater detail in the description, Figures and claims below.

The methods of treatment of the present invention involve the administration of a composition which features the IL6/sIL-6R complex, especially Hyper-IL-6. As described in further detail below, this complex is able to promote liver regeneration and the restoration of liver functions, and is able to significantly increase longevity when administered exogeneously to subjects suffering from liver injury. The background art has neither taught nor suggested any effect for the complex in subjects which do not express the components of the complex endogeneously. Furthermore, the background art has certainly neither taught nor suggested any effect for the complex when added exogeneously to subjects following liver injury. Thus, the effects of the composition and methods of the present invention are unexpected and are not taught or suggested by the background art.

According to the teachings of the present invention, there is provided a method for treating an injury to a liver of a subject, comprising the step of administering, to the subject, a pharmaceutically acceptable amount of an IL-6/sIL-6R complex in a pharmaceutically acceptable carrier, such that the injury to the liver is treated.

Preferably, the IL-6/sIL-6R complex includes Hyper-IL-6. Also preferably, the IL-6/sIL-6R complex is administered to the subject parenterally.

According to preferred embodiments of the present invention, the injury to the liver is selected from the group consisting of damage caused by a toxic substance, damage caused by mechanical trauma, damage caused by a malignancy, damage caused by an autoimmune pathological process, and damage caused by a pathogen. Preferably, the damage caused by the toxic substance includes alcoholic hepatitis and drug induced hepatopathology. Also preferably, the pathogen is a Hepatitis virus. Also preferably, the injury to the liver is selected from the group consisting of acute liver failure and chronic liver failure.

According to another embodiment of the present invention, there is provided a composition for treating an injury to a liver, comprising a pharmaceutically effective amount of an IL-6/sIL-6R complex in a pharmaceutically acceptable carrier, the pharmaceutically effective amount being an amount sufficient for treating the injury to the liver.

Preferably, the IL-6/sIL-6R complex is Hyper-IL-6.

Hereinafter, the term "injury to the liver" includes but is not limited to liver damage caused by toxic substances, by mechanical disruption or trauma, by a malignancy whether primary or metastasizing from another body tissue, by an autoimmune or other genetically-related pathological process, or by a pathogen such as any of the group of Hepatitis viruses. The term "injury to the liver" also encompasses acute or chronic liver failure, as well as conditions in which liver failure has not occured.

Hereinafter, the term "IL-6/sIL-6R complex" refers both to a bimolecular protein complex which features both the IL-6 polypeptide and sIL-6R, the soluble IL-6 receptor protein, and to a unimolecular protein which includes the bioactive portions of IL-6 and sIL-6R connected with a flexible linker, substantially as previously described in PCT Patent Application No. PCT/DE97/00458 and in Fischer, M. et al., Nature Biotech. 15, 142–145 (1997), incorporated by reference as if fully set forth herein, as well as any biologically active equivalents thereof.

Hereinafter, the term "Hyper-IL-6" refers to a unimolecular protein which includes the bioactive portions of IL-6 and sIL-6R connected with a flexible linker, substantially as previously described and shown in FIG. 1 of PCT Patent Application No. PCT/DE97/00458 (referred to as "H-IL-6" in that reference).

Hereinafter, the term "biologically active" refers to molecules, or complexes thereof, which are capable of exerting an effect in a biological system.

Hereinafter, the term "amino acid" refers to both natural and synthetic molecules which are capable of forming a peptidic bond with another such molecule. Hereinafter, the term "natural amino acid" refers to all naturally occurring amino acids, including both regular and non-regular natural amino acids. Hereinafter, the term "regular natural amino acid" refers to those amino acids which are normally used as components of a protein. Hereinafter, the term "non-regular natural amino acid" refers to naturally occurring amino acids, produced by mammalian or non-mammalian eukaryotes, or by prokaryotes, which are not usually used as a component of a protein by eukaryotes or prokaryotes. Hereinafter, the term "synthetic amino acid" refers to all molecules which are artificially produced and which do not occur naturally in eukaryotes or prokaryotes, but which fulfill the required characteristics of an amino acid as defined above. Hereinafter, the term "peptide" includes both a chain of a sequence of amino acids of substantially any of the above-referenced types of amino acids, and analogues and mimetics having substantially similar or identical functionality thereof.

With regard to the unimolecular protein, such as Hyper-IL-6, and the bimolecular protein complex, the expression "linker" relates to linkers of any kind, which are suitable for the binding of polypeptides. Examples of such linkers include but are not limited to bifinctional, chemical cross-linkers; a disulfide-bridge connecting two amino acids of both polypeptides; and a peptide or polypeptide.

The bimolecular protein complex includes both IL-6 and sIL-6R, as well as biologically active portions and variants thereof, connected by a linker. The term "variants" includes any homologous peptide to either IL-6 or sIL-6R, for example including any amino acid substitution or subsitutions which still maintain the biological activity of the original peptide or a polypeptide which directly stimulates the membrane receptor for the IL-6/sIL-6R complex which is called gp130.

The unimolecular protein can be a fusion polypeptide. For example, polypeptides featuring the bioactive portions of IL-6 and sIL-6R can be fused with each other and the linker can be a disulfide-bridge produced by the two polypeptides. Preferably the linker is a polypeptide, which connects the two other polypeptides with each other. These fusion polypeptides include a human sIL-6R-polypeptide, which is the extracellular subunit of an interleukin-6-receptor and a human IL-6-polypeptide, whereby the polypeptides are connected by different polypeptide-linkers with each other. The accession number for IL-6 is M14584 (GenBank Protein Sequences Database), and for the soluble IL-6 receptors is M57230 and M20566.

A variation of the unimolecular protein, which includes only amino acids 114–323 inclusive from the sIL-6R-polypeptide, is also included. A second variation includes amino acids 113–323 inclusive of the sIL-6R-polypeptide and amino acids 29–212 of the IL-6-polypeptide. Other variations and combinations as previously disclosed in PCT Patent Application No. PCT/DE97/00458 and in Fischer, M. et al., Nature Biotech. 15, 142–145 (1997) are also included in the unimolecular protein embodiment of the IL-6/sIL-6R complex.

Hereinafter, the term "treatment" includes both the amelioration or elimination of an existing condition and the prevention of the genesis of a condition. Hereinafter, the term "Hepatitis virus" includes any virus known to cause viral hepatitis including, but not limited to, Hepatitis A, B, C, D, E and other variants thereof

BRIEF DESCRIPTION OF THE DRAWINGS

The invention is herein described, by way of example only, with reference to the accompanying drawings, wherein:

FIG. 1 shows that Hyper-IL-6 causes an accelerated reconstitution of liver weight following partial hepatectomy in mice; immediately following a 50% partial hepatectomy, IL-6 (20 μg/mouse) or Hyper-IL6 (2 μg /mouse), or physiological saline was injected intraperitoneally into mice. At the time points indicated in the figure, mice were sacrificed, the remnant livers were removed and the percentage of liver weight increase compared to time 0 at hepatectomy was determined (see Methods). Four to six mice were operated at each time point in each treatment group. Mean values ± standard deviations are presented.

FIG. 2 shows that Hyper-IL-6 significantly accelerates liver proliferation in mice following partial hepatectomy; Following a 50% partial hepatectomy, IL-6 (20 μg/mouse) or Hyper-IL6 (2 μg /mouse), or physiological saline was injected intraperitoneally into mice. One hour before the mice were sacrificed, 50 mg/kg body weight BrdU in PBS was injected intraperitoneally into the mice. After removal of the remnant livers, the organs were fixed in 4% formaldehyde and embedded in paraffin. Tissue sections were subjected to BrdU immunohistochemistry. The percentage of BrdU-positive nuclei were counted in at least three mice per treatment group. Mean values ± standard deviation are shown.

FIG. 4 shows that the acute phase response is intact in mice following partial hepatectomy. Upper panel: 24 hours after intraperitoneal injection of saline, 20 μg IL-6 alone, or 2 μg Hyper-IL-6, blood was drawn from the animals which did not undergo partial hepatectomy. One μl of the murine serum was loaded on a 12.5% SDS gel and was subjected to SDS-PAGE. The gel was blotted onto a nitrocellulose membrane and was subjected to Western blotting using a monoclonal antibody specific for murine haptoglobin. Lower panel: Mice that had undergone partial bepatectomy were immediately treated with either saline, 20 μg IL-6, or with 2 μg Hyper-IL-6.24 hours after the operation, blood was drawn from the animals and serum was subjected to Western blotting as described above.

DETAILED DESCRIPTION OF THE PRESENT INVENTION

Figure 3:
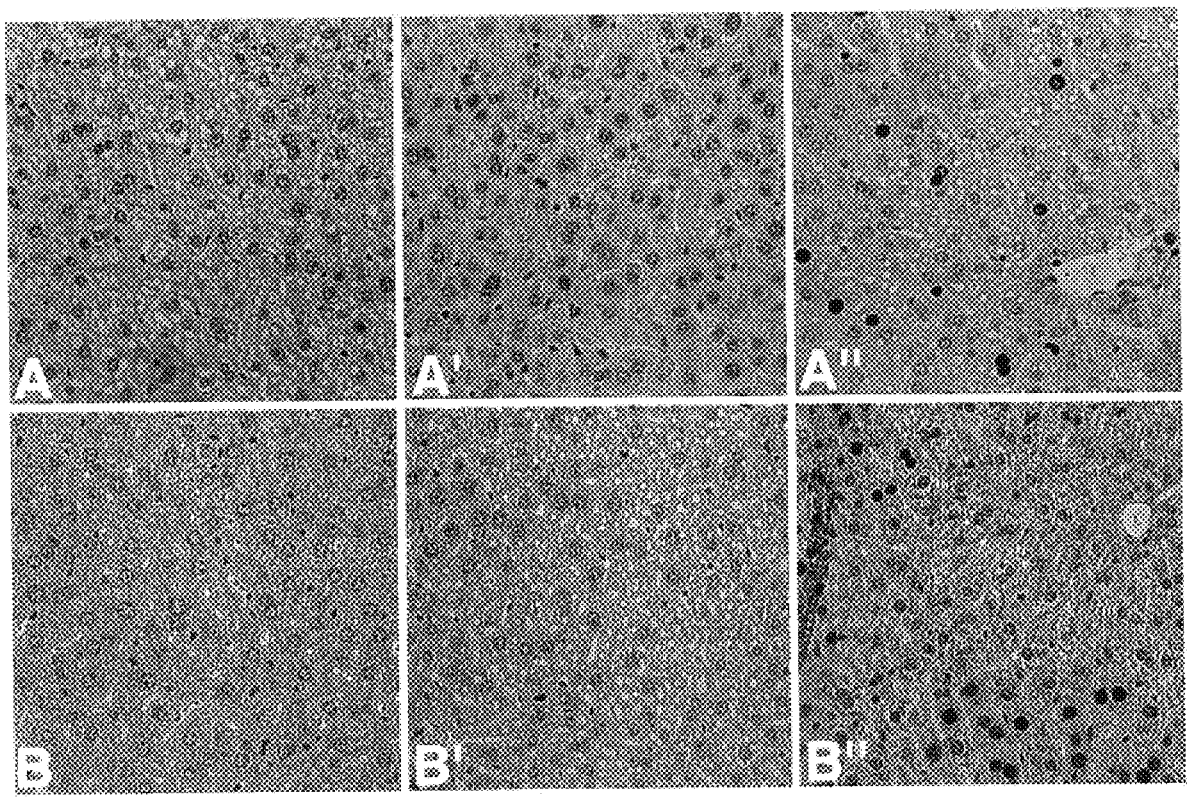
FIG. 3 shows BrdU labelling following partial hepatectomy in mice; Immunohistochemical detection of BrdU incorporation in S-phase liver nuclei as an indicator of liver cell proliferation. Following 50% partial hepatectomy, mice were either left untreated (A-C), treated with 20 μg IL-6/ mouse (A'-C'), or treated with 2 μg Hyper-IL-6 (A''-C''). Mice were sacrificed 24 hours (A, A', A''), 36 hours (B, B', B''), or 120 hours (C, C', C'') following surgery. One hour before the animals were sacrificed 50 mg/kg body weight BrdU in PBS was injected intraperitoneally. The bars represent 100 μm.

The present invention is drawn towards novel methods of use of the IL-6/sIL-6R complex, such as Hyper-IL-6. The IL-6/sIL-6R complex has now been shown to promote liver regeneration and the restoration of liver functions in subjects suffering from liver injury (see Example 1). Furthermore, administration of the IL-6/sIL-6R complex has now been shown to increase the lifespan of these subjects, as compared to untreated subjects (see Example 2). Thus, the IL-6/sIL-6R complex has significant utility for the treatment of many different types of liver diseases.

The principles and operation of the methods of treatment which feature IL-6/sIL-6R complex according to the present invention may be better understood with reference to the non-limiting illustrative examples below.

EXAMPLE 1

Effects of the IL-6/sIL-6R Complex in a Mouse Experimental Model

The effects of Hyper-IL-6 were examined in a mouse experimental model of liver damage. Two groups of mice underwent partial hepatectomy, in which a portion of the liver was removed, thereby seriously reducing overall liver functions. One group of mice received Hyper-IL-6, while a second, control group did not. The mice treated with Hyper-IL-6 showed and increased rate of liver regeneration and of a substantial restoration of liver functions. By contrast, the control mice showed a much slower rate of restoration of liver functions through liver regeneration. The experimental methods were as follows.

First, recombinant human IL-6[39] and Hyper-IL-6[19] were prepared as described in these references (39 and 19, respectively).

For partial hepatectomy, C57xBL/6 mice of 8 weeks old were obtained from the animal facility of the University of Mainz, Germany. In an initial experiment the relation between total body weight and liver weight was established in 20 mice. The mean total body weight was 27.45±1.25 g. The mean liver weight was 1.2±0.056 g. The mean ratio of liver weight (LW)/mean total body weight (BW) was 0.045.

Partial hepatectomy was performed as described by Higgins and Anderson[40]. Briefly, at the day of the operation, food was withdrawn at 8 AM in the morning and the surgery was carried out between 6 and 8 PM. Animals were anesthetized by an intraperitoneal injection of 2.5% avertin (mixture of 10 grams of tribromomethyl alcohol and 10 ml tertiary amyl alcohol). The total body weight of each mouse was recorded. The mice were then subjected to midventral laparotomy with an approximately 50% liver resection (left lateral and left half of medal lobes), slightly modified according to the procedure originally described by Higgins and Anderson[40]. The weight of the removed liver lobes was recorded. The weight of the residual liver lobes left behind was calculated by application of the formula 0.045=LW/BW. This weight was designated as "liver weight 1 at time 0". After the operation, the peritoneum was sutured and the skin was closed with wound clips.

Immediately after surgery, three groups, each including four to six mice, was subjected to one of three treatments: 2 μg Hyper-IL-6, 20 μg IL-6, or no treatment (control). All treatments were administered by injection; the control mice received an injection of physiological saline. After different time points as indicated in the figures, the mice were killed by cervical dislocation. The residual enlarged lobes were totally removed and their weight was recorded. This weight was designated as "liver weight 2 at time x". The percentage of the change, increase or decrease, in the weight of the liver after a defined period of time was calculated by subtracting liver weight 1 from liver weight 2.

In order to label the tissues with BrdU (5-bromo-2'-deoxyuridine), the animals were injected intraperitoneally with BrdU (50 mg/kg) (0.2% solution in PBS) one hour before the remnant liver was harvested and fixed. BrdU is a thymidine-analogue which is incorporated during the S-phase of the cell cycle into DNA. Applying immunhistochemical analyses using anti-BrdU-antibodies, S-phase-nuclei can be specifically detected. BrdU had been previously shown to be incorporated in S-phase-nuclei to the same extent as [3H]-Thymidine[20]. One hour after injection, the liver was then removed and immediately fixed in 4% paraformaldehyde (pH 7.2) at 4° C. An automated tissue processor was used to embed the livers in paraffin. Tissue sections (5 microns) were cut on a microtome and adhered to poly-lysine-coated glass slides. Staining of fixed tissue samples was carried out using an antibody to BrdU (Boehringer Mannheim) enabling proliferating cells (red nuclei) to be distinguished from quiescent ones (blue nuclei). The immunhistochemical study was performed as suggested by the manufacturer (BrdU labelling and detection kit by Boehringer Mannheim) and as described previously[41].

For the determination of haptoglobin protein determination in the serum, one microliter of murine serum was loaded on a 12.5 SDS gel and was subjected to SDS-PAGE gel analysis. The gel was blotted onto a nitrocellulose membrane and was subjected to Western blot analysis using a rabbit anti-human haptoglobin antibody (Dako, Glostrup, Denmark).

Results

The results demonstrated that Hyper-IL-6 causes an accelerated reconstitution of the liver weight following partial hepatectomy when compared to control mice and mice treated with IL-6, as shown in FIG. 1. Both untreated and IL-6-treated mice had a comparable increase of their liver weight. At 36 and 72 hours post surgery, IL-6-treated mice had slightly higher liver weights compared to untreated mice, which was not statistically significant. In Hyper-IL-6-treated mice, however, there was a dramatic increase of the liver weight at 72 and 120 hours post surgery ($p<0.005$). At 168 hours, the liver weights of all treatment groups had reached their baseline weight. These data demonstrate for the first time that the presence of the IL-6/sIL-6R-complex is able to significantly increase the liver weight restoration following partial removal of the liver. Most remarkably, IL-6 alone did not improve the rate of liver weight increase in mice in this experimental model.

FIG. 2 demonstrates that the increased rate of weight gain found in mice receiving Hyper-IL-6 treatment is caused by the significant acceleration of liver proliferation in these mice, when compared to control mice and mice receiving IL-6 treatment. Control and IL-6-treated animals showed a peak of BrdU-labelled cells at 72 and 120 hours post surgery. By contrast, in Hyper-IL-6 treated mice, the maximal percentage of BrdU-positive cells was detected as early as 24 and 36 hours post surgery. The difference was highly statistically significant. The results demonstrate that the presence of the IL-6/sIL-6R-complex markedly accelerates liver proliferation which results in the fast restoration of the liver weight.

FIG. 3 shows representative immunohistochemical studies after 50% partial hepatectomy (untreated (A-C), treated with 20 $\mu$g IL-6/mouse (A'-C'), or treated with 2 $\mu$g Hyper-IL-6 (A"-C"); sacrificed 24 hours (A, A', A"), 36 hours (B, B', B"), or 120 hours (C, C', C") following surgery). The bars represent 100 $\mu$m. As shown, control mice and IL-6-treated mice do not have any BrdU-positive cells detectable at 24 and 36 hours post surgery. However, at these time points, in Hyper-IL-6-treated mice, there is a high number of BrdU-labelled cells.

FIG. 4 shows that the hepatic acute phase protein production is intact after partial hepatectomy, as determined by analysis of the serum haptogiobin concentration by Western blot analysis in blood samples. First, the serum haptoglobin concentrations were measured in serum samples from mice which did not undergo partial hepatectomy. These mice were injected with saline, IL-6 alone (20 $\mu$g), or Hyper-IL-6 (2 $\mu$g). The upper panel of FIG. 4 shows that 24 hours after injection, IL-6 treatment alone leads to some slight haptoglobin protein increase in the serum, whereas the treatment with Hyper-IL-6 resulted in a marked elevation of the haptoglobin concentration in the serum. The haptoglobin mRNA concentration in the liver corresponds with the protein data shown in FIG. 4 (data not shown).

When the haptoglobin serum concentration was determined in hepatectomized mice 24 hours following the operation, mice receiving saline injections also had a slight haptoglobin protein elevation in their serum when compared to mice which did not undergo hepatectomy. The treatment with IL-6 alone and with Hyper-IL-6 resulted in a comparable serum haptoglobin concentration when compared to mice which did not undergo hepatectomy (FIG. 4, lower panel). These data show that the regenerating liver is capable of mounting a normal acute phase protein response.

These data have demonstrated for the first time that in the presence of IL-6 and its soluble receptor, sIL-6R, liver regeneration in mice following partial hepatectomy is greatly accelerated. Moreover, the IL-6/sIL-6R complex has now been shown to rapidly cause hepatocyte proliferation of the liver following partial hepatectomy in mice. IL-6 alone at a ten-fold higher dosage than the designer cytokine Hyper-IL-6 did not cause accelerated liver regeneration or hepatocyte proliferation as compared to untreated animals. Thus, only Hyper-IL-6 was able to induce liver regeneration and the restoration of liver functions in mice which had undergone partial hepatectomy.

EXAMPLE 2

Survival of Rats with Hepatatic Failure

In order to assess the ability of Hyper-IL-6 to treat fulminant hepatatic failure (FHF), FHF was induced in four rats. Two also received Hyper-IL-6, one received hepatocytes and one received human IL-6 alone. The rats which received Hyper-IL-6 survived for over one month, while the other rats died within 24–72 hours. The experimental method was as follows.

Four male Sprague-Dawley rats were deprived of food, but not of drinking water, for 12 hours. Next, the rats were injected i.p. with D-Galactosamine (1.4 g/kg, pH=6.8). After 24 hours of D-Galactosamine treatment, fulminant hepatic failure was induced. Two rats then received Hyper-IL-6 (7 micrograms, i.p.). One rat received human IL-6 (80 micrograms, i.p.). One rat received a transplantation of syngeneic hepatocytes ($2\times10^5$ cells).

The rat which received human IL-6 died 24 hours after treatment, while the rat which received the hepatocyte transplant died within 72 hours. Only the animals treated with Hyper-IL-6 survived for over one month before being sacrificed. Thus, Hyper-IL-6 was clearly able to prolong the life-span of rats suffering from hepatic failure.

EXAMPLE 3

Compositions and Methods of Treatment with Hyper-IL-6

As described previously in the section entitled "Summary of the Invention", the term "IL-6/sIL-6R complex" refers to a bimolecular protein complex which features both the IL-6 polypeptide and sIL-6R, the soluble IL-6 receptor protein; and to a unimolecular protein which includes the bioactive portions of IL-6 and sIL-6R connected with a flexible linker, as previously described in PCT Patent Application No. PCT/DE97/00458, and in Fischer, M. et al., *Nature Biotech.* 15, 142–145 (1997), as well as pharmaceutically acceptable salts thereof.

The composition containing the IL-6/sIL-6R complex, and in particular Hyper-IL-6, can be administered to a subject in a number of ways, which are well known in the art. Hereinafter, the term "subject" refers to the human or lower animal to whom Halofuginone was administered. For example, administration may be done topically (including ophtalmically, vaginally, rectally, intranasally and by inhalation), orally, or parenterally, for example by intravenous drip or intraperitoneal, subcutaneous, or intramuscular injection.

Particularly preferred routes of administration include parenteral, intranasal and by inhalation.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the IL-6/sIL-6R complex, as well as on the particular embodiment administered. Persons of ordinary skill in the art can easily determine optimum dosages, dosing methodologies and repetition rates.

As noted previously, the compositions found to be useful in the methods of the present invention include the IL-6/sIL-6R complex. The methods of the present invention are useful for the treatment of injury to the liver. The following example is an illustration only of a method of treating such an injury to the liver, and is not intended to be limiting in any way.

The method includes the step of administering the composition including the IL-6/sIL-6R complex, in a pharmaceutically acceptable carrier as described above, to a subject to be treated. The composition preferably features Hyper-IL-6 as the embodiment of the IL-6/sIL-6R complex. The composition is administered according to an effective dosing methodology, preferably until a predefined endpoint is reached, which could include one or more of the following: a normalized level of coagulation factors 5 or 7; normalized prothrombin time; the absence of hepatic encephalopathy; normalized levels of liver enzymes such as aspartate aminotransferase and alanine aminotransferase; and normalized ammonia levels.

In a preferred embodiment of the method of the present invention, the composition including the IL-6/sIL-6R complex is administered to a subject before, during or after liver transplantation, or a combination of these timepoints of administration thereof, in order to promote growth and regeneration of the transplanted liver.

Examples of injuries to the liver for which such a method of treatment would be suitable include but are not limited to liver damage caused by toxic substances, including alcoholic hepatitis and drug induced hepatopathy; damage caused by mechanical disruption or trauma; damage caused by a malignancy, whether primary or metastasizing from another body tissue; damage caused by an autoimmune or other genetically-related pathological process; and damage caused by a pathogen such as any of the group of Hepatitis viruses, including dominant viral hepatitis. The term "injury to the liver" also encompasses acute or chronic liver failure, including fulminant hepatic failure, as well as conditions in which liver failure has not occured, including any condition featuring a reduction of liver functions from a substantially normal level.

The term "treating" includes ameliorating, alleviating or substantially eliminating a liver injury, as well as substantially preventing a liver injury.

While the invention has been described with respect to a limited number of embodiments, it will be appreciated that many variations, modifications and other applications of the invention may be made.

What is claimed is:

1. A method for treating an injury to a liver of a subject, comprising the step of administering, to the subject, a pharmaceutically acceptable amount of an IL-6/sIL-6R complex in a pharmaceutically acceptable carrier, such that the injury to the liver is treated.

2. The method of claim 1, wherein said IL-6/sIL-6R complex is Hyper-IL-6.

3. The method of claim 1, wherein said IL-6/sIL-6R complex is administered to the subject parenterally.

4. The method of claim 1, wherein the injury to the liver is selected from the group consisting of reduction of liver function from a normal level caused by a toxic substance, reduction of liver function from a normal level caused by mechanical trauma, reduction of liver function from a normal level caused by a malignancy, and reduction of liver function from a normal level caused by a pathogen.

5. The method of claim 4, wherein said reduction of liver function from a normal level caused by said toxic substance includes alcoholic hepatitis and drug induced hepatopathy.

6. The method of claim 4, wherein said pathogen is a Hepatitis virus.

7. The method of claim 4, wherein the injury to the liver is selected from the group consisting of acute liver failure and chronic liver failure.

* * * * *